(12) United States Patent
Chen et al.

(10) Patent No.: US 7,547,473 B2
(45) Date of Patent: Jun. 16, 2009

(54) MAGNETIC NANOPARTICLES AND METHOD FOR PRODUCING THE SAME

(75) Inventors: Dong-Hwang Chen, Tainan (TW); Yang-Chuang Chang, Banqiao (TW)

(73) Assignee: National Cheng Kung University, Tainan (TW)

( * ) Notice: Subject to any disclaimer, the term of this patent is extended or adjusted under 35 U.S.C. 154(b) by 496 days.

(21) Appl. No.: 11/283,170

(22) Filed: Nov. 18, 2005

(65) Prior Publication Data
US 2007/0116955 A1    May 24, 2007

(51) Int. Cl.
B32B 5/66    (2006.01)
(52) U.S. Cl. .................. 428/403; 428/404; 428/405; 428/406; 428/407; 428/694 BA; 427/212
(58) Field of Classification Search ................ 428/403, 428/404, 405, 406, 407, 694 BA; 427/212
See application file for complete search history.

(56) References Cited

U.S. PATENT DOCUMENTS 4,285,819 A * 8/1981 Yen et al. .................... 210/679

FOREIGN PATENT DOCUMENTS

TW    224025 B    4/2003

OTHER PUBLICATIONS

Chang et al, "Preparation and adsorption properties of monodisperse chitosan-bound magnetic nanoparticles for removal of Cu(II) ions". JC&IS, Sep. 9, 2004.*

Yang-Chuang Chang et al., "Preparation and Adsorption Properties of Monodisperse Chitosan-Bound $FE_3O_4$ Magnetic Nanoparticles for Removal of Cu(II) Ions", *Journal of Colloid and Interface Science 283* (2005), Sep. 9, 2004, pp. 446-451.

Yang-Chuang Chang et al., "Monodisperse Chitosan-bound $FE_3O_4$ Nanoparticles With and Without Adsorbing Gd Ions as MRI Contrast Agents", pp. 109-111.

Hiroyuki Honda et al., "Development of Chitosan-Conjugated Magnetite for Magnetic Cell Separation", *Journal of Fermentation and Bioengineering*, vol. 86, No. 2, 1998, pp. 191-196.

Yang-Chuang Chang et al., "Adsorption Kinetics and Thermodynamics of Acid Dyes on a Carboxymethylated Chitosan-Conjugated Magnetic Nano-Adsorbent", *Macromolecular Bioscience*, Jan. 25, 2005, pp. 254-261.

Yang-Chuang Chang et al., "Conjugation of Monodisperse Chitosan-Bound Magnetic Nanocarrier with Epirubicin for Targeted Cancer Therapy", *Journal of Biomedical Nanotechnology*, vol. I, 2005, pp. 1-6.

Yang-Chuang Chang et al., Magnetic Chitosan Nanoparticles: Studies on Chitosan Binding and Adsorption of Co(II) Ions, Reactive and Functional Polymers, Jul. 9, 2005.

* cited by examiner

*Primary Examiner*—Leszek Kiliman
(74) *Attorney, Agent, or Firm*—Kinney & Lange, P.A.

(57) ABSTRACT

Magnetic nanoparticles and a method for producing the same are disclosed. A carboxylated polysaccharide with various functions such as chelating and ion exchange is covalently bound on the surfaces of magnetic nanoparticles. The polysaccharide-bound magnetic nanoparticles are highly stable, well dispersed, and have many advantages of high adsorption capacity, fast adsorption rate and easy magnetically manipulation. Hence, the polysaccharide-bound magnetic nanoparticles are applied to adsorb many ionic substances, and further act as an adsorbent for wastewater treatment or biochemical separation, a carrier for drugs or gene site-directed delivery, and a magnetic resonance imaging (MRI) contrast agent.

9 Claims, 5 Drawing Sheets

MAGNETIC NANOPARTICLES AND METHOD FOR PRODUCING THE SAME

FIELD OF THE INVENTION

The present invention relates to magnetic nanoparticles and method for producing the same, and more particularly, to polysaccharide-bound magnetic nanoparticles and method for producing the same.

BACKGROUND OF THE INVENTION

Magnetic nanoparticles are useful for a wide range of applications including high-density data storage, magnetic fluid, MRI (magnetic resonance image) contrast agent, separation processes, and biomedicine. Surface modification of nanoparticles with synthetic or natural polymer not only improves the dispersity and the stability of the nanoparticles, but also can be used to create complex nanoparticles with magnetic and polymer functionality. Chitosan is a natural biopolymer capable of chelating heavy metal ions, and adsorbing anions through ion exchange. In addition to typical adsorption separation, chitosan has great potential applications in biomedicine by forming complex with drugs, enzymes, proteins or DNA.

H. Honda et al. (*J. Ferment. Bioeng*, 86, 191 (1998)) disclose a method for preparing chitosan-conjugated magnetic particles by adding chitosan during the coprecipitation process of preparing iron oxide magnetic nanoparticles and binding chitosan to the iron oxide magnetic nanoparticles through coupling agents and cross-linkers. However, since the resultant magnetic composites are either aggregated or unstable due to polymer cross-linking or physisorption, the particle sizes become above 100 nm, even larger than 1000 nm. Therefore, monodisperse chitosan-$Fe_3O_4$ complex nanoparticles with particle sizes less than 100 nm cannot be obtained by the conventional method.

The present inventors, in Taiwan patent application Ser. No. 92108178, disclose a cationic magnetic nano-adsorbent prepared by covalently binding polyacrylic acid to the surface of iron oxide magnetic nanoparticles. This nano-adsorbent possesses the advantages of high adsorption capacity, fast adsorption rate, and easy magnetically manipulation, but is not suitable for anionic substances and multivalent heavy metal ions.

Briefly, chitosan or composite particles thereof are typically used in microscale or submicroscale application. Although they may be prepared as particles with diameter of a few tens of nanometers by microemulsification, it is quite difficult to purify the resultant product.

Accordingly, there is a need for magnetic nanoparticles and a method for producing the same which improves upon the drawbacks associated with the conventional process, e.g., larger particle size, particle aggregation or instability, purification difficulties, or limited application range.

SUMMARY OF THE INVENTION

It is an object of the present invention to provide magnetic nanoparticles and a manufacturing method thereof. In the present invention, a carboxylated polysaccharide with various functions such as chelating and ion exchange is covalently bound on the surface of magnetic nanoparticles. The polysaccharide-bound magnetic nanoparticles are highly stable, well dispersed, and have chelating or ion exchange functions. Therefore, they can be used to adsorb many ionic substances such as metal cations, anionic species, drug molecules and biomolecules, and further act as an adsorbent for wastewater treatment or biochemical separation, a carrier for drugs or gene site-directed delivery, and a magnetic resonance imaging (MRI) contrast agent.

According to the above and other objects of the present invention, there is provided polysaccharide-bound magnetic nanoparticles each comprising a carboxylated polysaccharide covalently bound to the surface of a magnetic nanoparticle, wherein the magnetic nanoparticle may be made of $Fe_3O_4$, and the carboxylated polysaccharide may be a carboxylated chitosan or derivative thereof such as carboxylated chitin for adsorbing ionic substances such as metal cations, anionic species, drugs and biomolecules.

According to one embodiment of the present invention, the polysaccharide-bound magnetic nanoparticles mentioned above have a diameter between 1 nm and 100 nm, preferably between 10 nm and 30 nm.

According to the above and other objects of the present invention, there is provided a method for producing the polysaccharide-bound magnetic nanoparticles. Firstly, $Fe_3O_4$ magnetic nanoparticles are formed from a solution of ferrous chloride and ferric chloride by co-precipitation or other methods. Then, carboxylated polysaccharides or derivative thereof are covalently bound to the surface of the magnetic nanoparticles through activation with carbodiimide. The carboxylated polysaccharide may be a carboxylated chitosan or derivative thereof such as carboxylated chitin.

The polysaccharide-bound magnetic nanoparticles of the present invention may be used to adsorb ionic substances. Firstly, a polar solution containing the ionic substances is mixed with the polysaccharide-bound magnetic nanoparticles for adsorbing the ionic substances. Then, a magnetic field is applied to separate out the polysaccharide-bound magnetic nanoparticles with the ionic substances adsorbed thereon.

In addition, the polysaccharide-bound magnetic nanoparticles of the present invention may be used as a carrier for the transport of drug molecules or biomolecules. Firstly, a polar solution containing the drug molecules and/or biomolecules is mixed with the polysaccharide-bound magnetic nanoparticles for with the drug molecules and/or biomolecules adsorbed thereon. Then, a magnetic field is applied to direct the polysaccharide-bound magnetic nanoparticles with the drug molecules and/or biomolecules adsorbed thereon to a predetermined position in vitro or in vivo.

The polysaccharide-bound magnetic nanoparticles of the present invention overcome the drawback of larger particle size associated with conventional techniques and possess the advantages of high adsorption capacity, fast adsorption rate, and easy magnetically manipulation. Therefore, the polysaccharide-bound magnetic nanoparticles of the present invention can act as an adsorbent for wastewater treatment or biochemical separation, a carrier for drugs or gene site-directed delivery, and a magnetic resonance imaging (MRI) contrast agent.

BRIEF DESCRIPTION OF THE DRAWINGS

Other objects, advantages, and novel features of the invention will become more apparent from the following detailed description when taken in conjunction with the accompanying drawing.

DETAILED DESCRIPTION OF THE PREFERRED EMBODIMENT

Figure 1A:
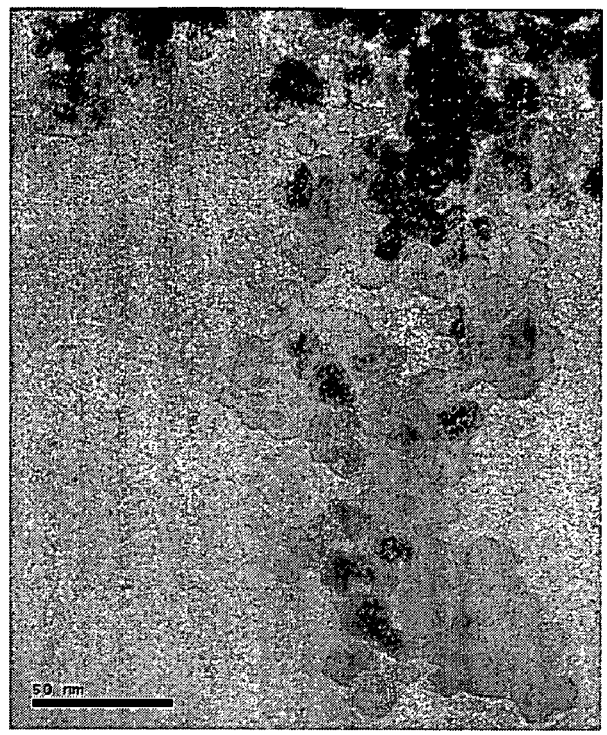
FIG. 1A shows a TEM micrograph for the carboxylated chitosan-bound magnetic nanoparticles of Example 1.
Figure 1B:
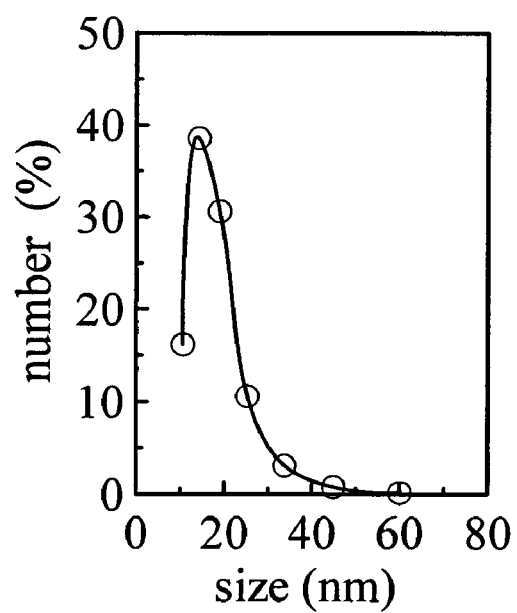
FIG. 1B shows the DLS result of the carboxylated chitosan-bound magnetic nanoparticles of Example 1.

The present invention is directed to magnetic nanoparticles and a method for producing the same, wherein a carboxylated polysaccharide with various functions such as chelating and ion exchange is covalently bound on the surfaces of magnetic nanoparticles. The polysaccharide-bound magnetic nanoparticles are highly stable, well dispersed, and have many advantages of high adsorption capacity, fast adsorption rate and easy magnetically manipulation. Hence, the polysaccharide-bound magnetic nanoparticles may be applied to adsorb many ionic substances such as metal cations, anionic species, drug molecules and biomolecules. The magnetic nanoparticles and method for producing the same are described in detail below.

Firstly, $Fe_3O_4$ magnetic nanoparticles are formed from a solution of ferrous chloride and ferric chloride by co-precipitation or other methods. Taking co-precipitation as an example, ferric and ferrous chlorides (molar ratio 1.5-2.5:1, preferably 2:1) were dissolved in solvent to form an iron-containing solution. Thereafter, an alkaline solution such as an ammonium solution (29.6%) is added to adjust the iron-containing solution's pH to between 8 and 10, and then the iron-containing solution is heated at a temperature between 60. and 80. for 1-60 min to obtain magnetic nanoparticles of $Fe_3O_4$. Finally, the magnetic nanoparticles are washed several times with deionized water and dried for subsequent treatment.

Next, a carboxylation process is conducted by a swelling and alkalizing step. Specifically, polysaccharide such as chitosan or chitin is added into an alkaline mixture of organic solvent, water and sodium hydroxide at a temperature between 55. and 65. for 0.5-1.5 h. In one embodiment of the present invention, the organic solvent may be isopropyl alcohol which may be mixed with water in a volume ratio of 4. Then, an organic solvent (such as isopropyl alcohol) containing monochloroacetic acid solution is added into the alkaline mixture containing polysaccharide in drops at a temperature between 55. and 65. to form carboxylated polysaccharide such as carboxymethylated chitosan (CMCH) or the derivative thereof such as carboxylated chitin. After reaction for 3-5 h, ethyl alcohol (70%) is added to stop the carboxylation reaction. Then, the carboxylated polysaccharide is rinsed with 99% ethyl alcohol to desalt and dewater, and dried in an oven for subsequent treatment.

Thereafter, the magnetic nanoparticles, the carboxylated polysaccharide, and the carbodiimide are added successively to a buffered solution such as phosphate-buffered saline (PBS) having a pH in the range of about 6 to about 7 (0.003 M). Through carbodiimide activation of the carboxyl group of the carboxylated polysaccharide and the hydroxyl group on the surface of the magnetic nanoparticle, the carboxylated polysaccharide is covalently bound to the surface of the magnetic nanoparticle. In order to make the entire surface of each magnetic nanoparticle fully covered by the carboxylated polysaccharide, the weight ratio of the carboxylated polysaccharide to the $Fe_3O_4$ nanoparticle in the buffered solution is at least about 0.05.

Finally, liquid-solid separation is conducted by applying a magnetic field, e.g., by using a permanent magnet with a surface magnetization of 6000 G.T, in order to obtain the polysaccharide-bound magnetic nanoparticles. In one embodiment, the polysaccharide-bound magnetic nanoparticles have a diameter between 1 nm and 100 nm, preferably between 10 nm and 30 nm.

Note that the present invention is characterized by covalently binding carboxylated polysaccharides or derivative thereof to the surface of the magnetic nanoparticles through activation with carbodiimide. The resultant polysaccharide-bound magnetic nanoparticles overcome the drawback of larger particle size associated with conventional techniques and possess the advantages of high adsorption capacity, fast adsorption rate, and easy magnetically manipulation. In addition, the carboxylated polysaccharide or the derivative thereof has various functions such as chelating and ion exchange. Therefore, the polysaccharide-bound magnetic nanoparticles of the present invention can act as an adsorbent for wastewater treatment or biochemical separation, a carrier for drugs or gene site-directed delivery, and a magnetic resonance imaging (MRI) contrast agent.

Examples of the magnetic nanoparticles, methods for producing the same, and applications thereof will now be described in conjunction with the accompanying FIGS. 1-9, but the present invention should not be construed as being limited thereto.

EXAMPLE 1

The synthetic sequences of chitosan-bound magnetic nanoparticles are outlined in Scheme 1.

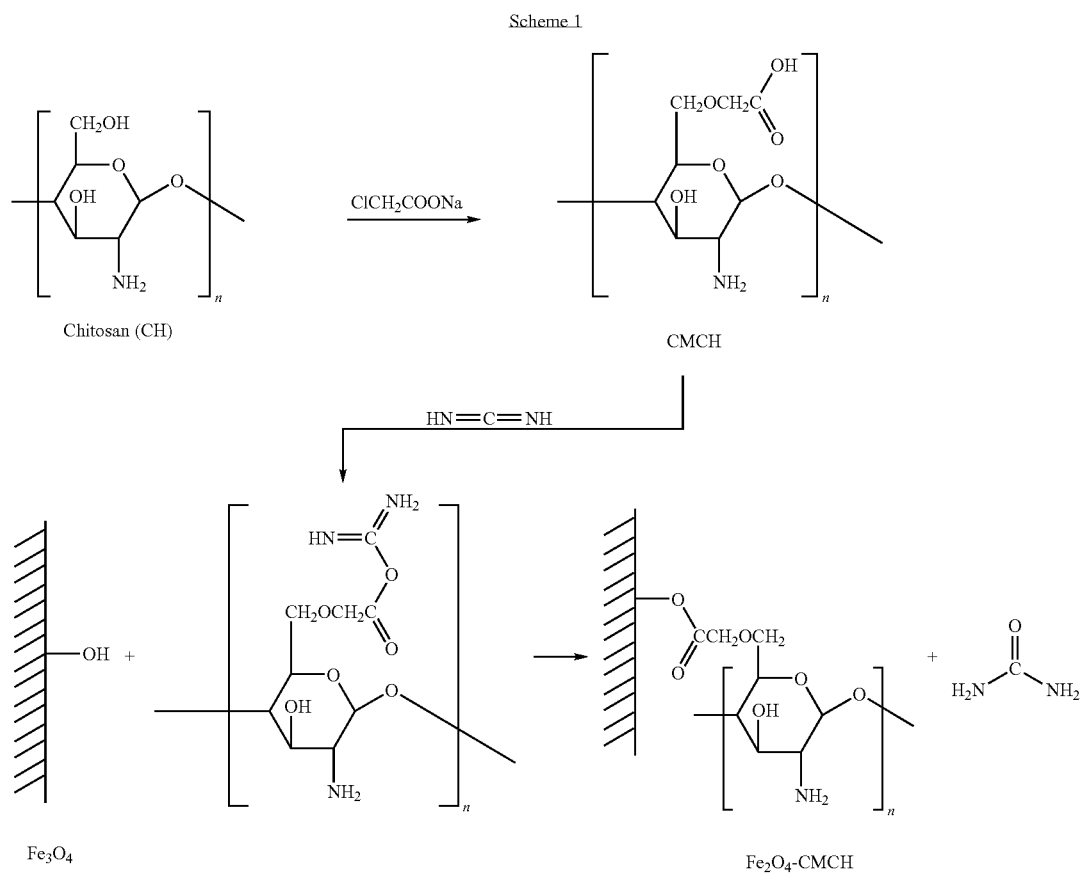

Ferric and ferrous chlorides (molar ratio 2□1) were dissolved in water to form an iron-containing solution. An ammonium solution (29.6%) is added to adjust the iron-containing solution's pH to 10, and then the iron-containing solution is heated at 80. for 30 min to obtain magnetic nanoparticles of $Fe_3O_4$. Finally, the magnetic nanoparticles are washed several times with deionized water and dried for subsequent treatment.

Next, 15 g of sodium hydroxide and 3 g of chitosan were added into 100 ml of isopropyl alcohol/water (80/20) mixture at 60. to swell and alkalize for 1 h. Then, 20 ml of monochloroacetic acid solution (0.75 g/ml in isopropyl alcohol) was added into the mixture containing chitosan in drops in 30 min. After reaction for 4 h at 60., 200 ml of ethyl alcohol (70%) was added to stop the reaction. The solid was filtered, rinsed with 70% and 99% ethyl alcohol to desalt and dewater, and dried in an oven at 50. thereby obtaining the carboxylated chitosan.

The binding of carboxylated chitosan onto magnetic nanoparticles was conducted as follows. First, 100 mg of magnetic nanoparticles were added to 2 ml of buffer A (0.003 M phosphate, pH 6, 0.1 M NaCl). Then, the reaction mixture was sonicated for 10 min after adding 0.5 ml of carbodiimide solution (0.025 g/ml in buffer A). Finally, 2.5 ml of carboxylated chitosan solution (50 mg/ml in buffer A) was added and the reaction mixture was sonicated for 60 min. Finally, liquid-solid separation is conducted by applying a magnetic field, e.g., by using a permanent magnet with a surface magnetization of 6000 G.T, in order to obtain the carboxylated chitosan-bound magnetic nanoparticles which were settled within 1-2 min and then were washed with water and ethanol.

The core diameter and crystal structure of the resultant chitosan-bound magnetic nanoparticles were observed by transmission electron microscopy (TEM), dynamic light scattering (DLS) analysis, and X-ray diffraction (XRD). X-ray diffraction (XRD) measurement was performed using CuKa radiation with a scanning rate of 4°/m in 2. ranged from 20' to 70'.

FIG. 1 A shows a TEM micrograph for the carboxylated chitosan-bound magnetic nanoparticles of Example 1. As shown, the resultant chitosan-bound magnetic nanoparticles are essentially monodisperse and have a quite even diameter. All of the diameters of the carboxylated chitosan-bound magnetic nanoparticles are in the nanoscale, i.e., 1-100 nm, and the mean diameter is about 13 nm.

Furthermore, the dynamic light scattering (DLS) result (see FIG. 1B) shows that the carboxylated chitosan-bound magnetic nanoparticles are monodisperse and have a hydrodynamic diameter of 17.1 nm, hence, the carboxylated chitosan-bound magnetic nanoparticles show good monodispersity. Thus, the covalently binding between chitosan and magnetic nanoparticle does not significantly result in particle agglomeration.

Figure 2:
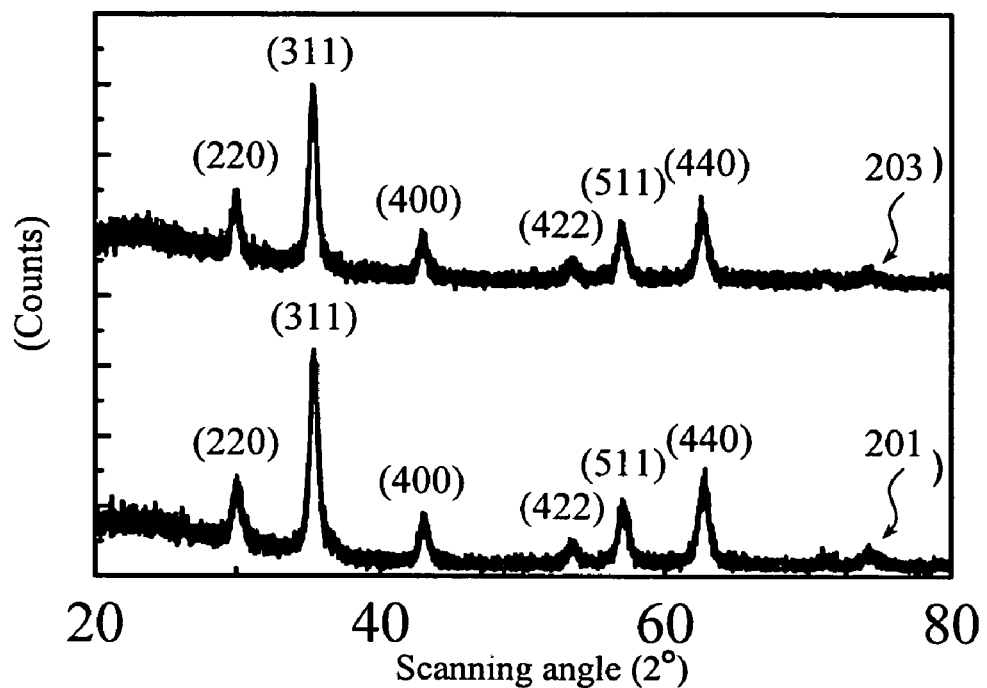
FIG. 2 shows the XRD patterns for naked magnetic nanoparticles and for the chitosan-bound magnetic nanoparticles.

FIG. 2 shows an XRD pattern 201 for naked magnetic nanoparticles and an XRD pattern 203 for the chitosan-bound magnetic nanoparticles. Six characteristic peaks for $Fe_3O_4$ (2.=30.1, 35.5, 43.1, 53.4, 57.0, and 62.6°), marked by their indices ((220), (311), (400), (422), (511), and (440)), are observed for both samples. These peaks reveal that the resultant nanoparticles were pure $Fe_3O_4$ with a spinel structure. It is explained that the binding process did not result in the phase change of $Fe_3O_4$.

Magnetic measurement of the carboxylated chitosan-bound magnetic nanoparticles of Example 1 was done using a superconducting quantum interference device (SQUID) magnetometer with a magnetization between −30000 and +30000 G.T. The magnetic measurement indicated that the carboxylated chitosan-bound magnetic nanoparticles are superparamagnetic and the saturation magnetization (Ms), remanent magnetization (Mr), coercivity (Hc), and squareness (Sr=Mr/Ms) thereof are 61.7 emu/g, 0.82 emu/g, 8.5 Oe, and 0.013, respectively.

The Fourier transform infrared (FTIR) spectra of chitosan (curve 301), the carboxylation product of chitosan (curve 303), magnetic nanoparticles (curve 305), and the carboxylated chitosan-bound magnetic nanoparticles (curve 307) were analyzed on a FTIR spectrometer.

Figure 3:
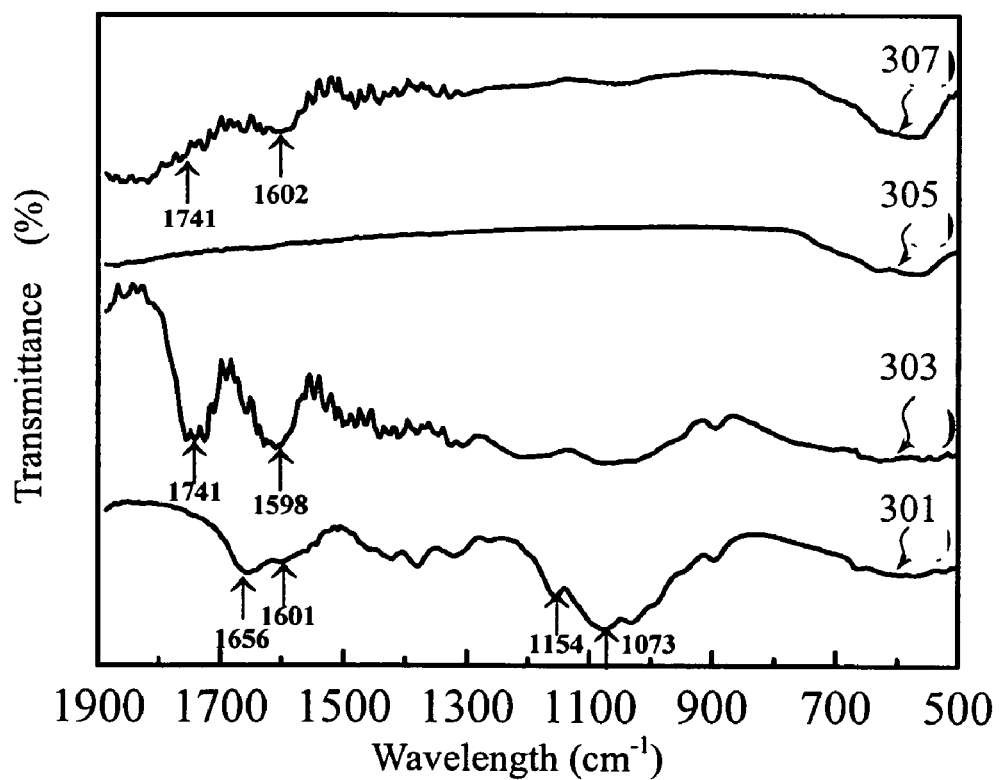
FIG. 3 shows FTIR spectra of chitosan, carboxylation product of chitosan, magnetic nanoparticles, and the carboxylated chitosan-bound magnetic nanoparticles of Example 1.

As shown in FIG. 3, two main characteristic peaks of chitosan (curve 301) at 1601 $cm^{-1}$ and 1651 $cm^{-1}$ (corresponding to $—NH_2$ and $—NH^{3+}$, respectively) are observed. Two main characteristic peaks of the carboxylation product of chitosan (curve 303) at 1598 $cm^{-1}$ and 1741 $cm^{-1}$ (corresponding to the amino and carboxyl groups, respectively) are observed, revealing the formation of carboxylated chitosan. No characteristic peaks of magnetic nanoparticles (curve 305) are observed. The characteristic peak of the carboxylated chitosan-bound magnetic nanoparticles (curve 307) at 1602 $cm^{-1}$ is resulted from the amino groups of chitosan, revealing that the carboxylated chitosan is indeed bound on the surface of magnetic nanoparticle. Curve 307 further shows that the characteristic peak resulted from the carboxyl groups of carboxylated chitosan at 1741 $cm^{-1}$ become quite weak. This may be attributed to the depletion of carboxyl groups in the binding reaction.

Figure 4:
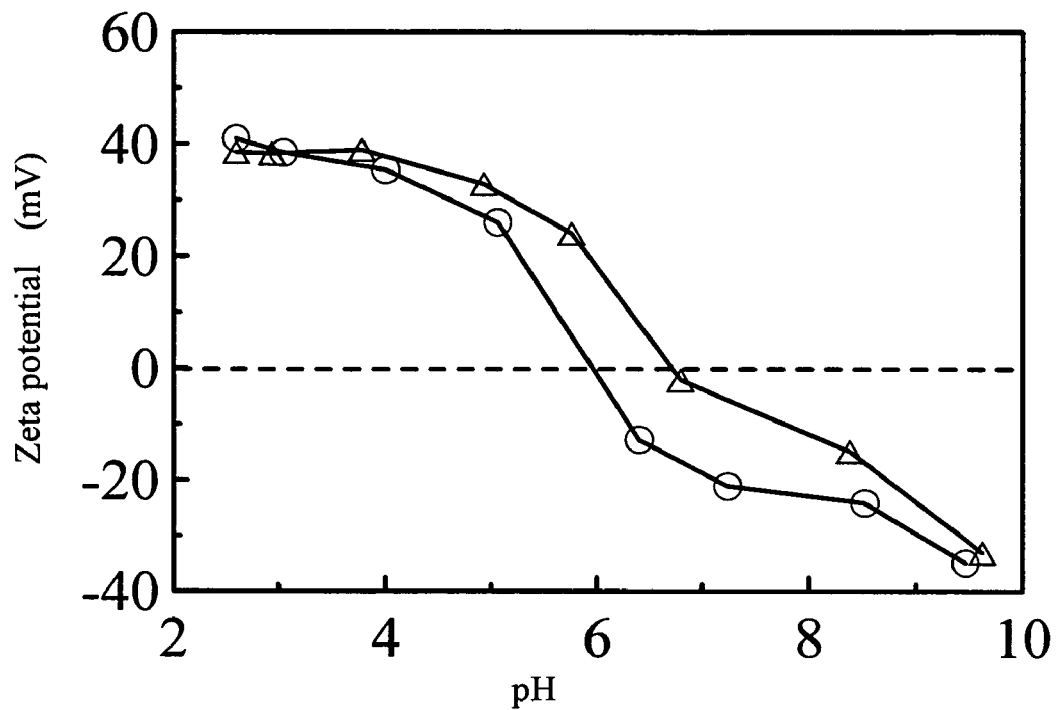
FIG. 4 shows the zeta potentials of the magnetic nanoparticles and the carboxylated chitosan-bound magnetic nanoparticles of Example 1.

The binding of chitosan is also demonstrated by the measurement of zeta potential. FIG. 4 shows the zeta potentials of the magnetic nanoparticles (as indicated by .) and the carboxylated chitosan-bound magnetic nanoparticles (as indicated by .). As shown, the isoelectric point (pI) of the magnetic nanoparticles is about 6.8. The isoelectric point (pI) of the carboxylated chitosan-bound magnetic nanoparticles is shifted to 5.95. This also confirms the binding of the carboxylated chitosan on the surface of magnetic nanoparticle.

The amount of carboxylated chitosan bound on the magnetic nanoparticles (100 mg) is 5.25 mg which is determined from the increased weight after chitosan binding. The carboxylated chitosan binding amount may also be determined by the spectrophotometric assay based on the reaction of amino groups with an excess of o-phthaldialdehyde (OPA) and subsequent quantitative determination of unreacted OPA by reaction with glycine. The result of the spectrophotometric assay shows that 5.08 mg carboxylated chitosan is bound on 100 mg magnetic nanoparticles. This is in agreement with that obtained from the weight difference. Furthermore, the spectrophotometric analysis also reveals that substantially all of the amino groups of the carboxylated chitosan remain intact and are not destroyed by the binding of the carboxylated chitosan to the magnetic nanoparticles.

The carboxylated chitosan-bound magnetic nanoparticles can be used to adsorb many ionic substances such as metal cations or anionic species.

EXAMPLE 2

The feasibility of carboxylated chitosan-bound magnetic nanoparticles as a magnetic nano-adsorbent for the removal of heavy metal ions from aqueous solutions was demonstrated using $Co^{2+}$ and $Cu^{2+}$ ions as model compounds. The typical adsorption experiments were conducted at pH 3-5 under a constant temperature of 25. by mixing a polar solution containing the ionic substances with the carboxylated chitosan-bound magnetic nanoparticles for adsorbing the ionic substances. Then, a magnetic field was applied to separate out the carboxylated chitosan-bound magnetic nanoparticles with the ionic substances adsorbed thereon.

Figure 5:
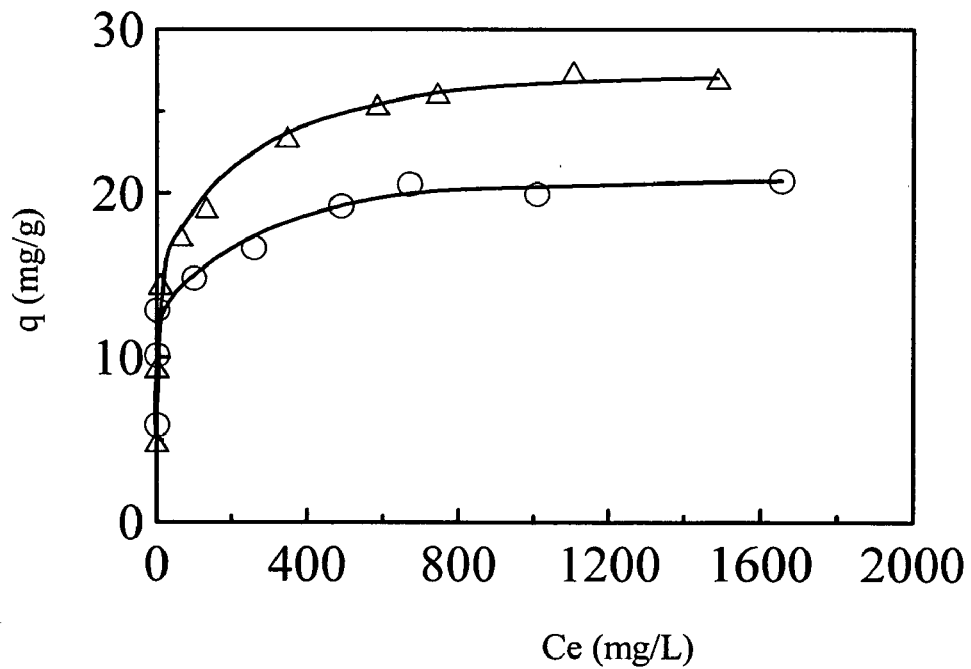
FIG. 5 shows equilibrium isotherms for the adsorption of Cu(II) ions and cobalt ions on the carboxylated chitosan-bound magnetic nanoparticles.

FIG. 5 shows equilibrium isotherms for the adsorption of Cu(II) ions (as indicated by .) and cobalt ions (as indicated by .) on the carboxylated chitosan-bound magnetic nanoparticles wherein Ce is the equilibrium concentration in solution (mg/L) and q is the adsorption capacity (mg/g). As shown, the adsorption capacity increases with the initial concentration, the maximum adsorption capacity for Cu(II) ions is 21.5 mg/g, and the maximum adsorption capacity for cobalt ions is 27.46 mg/g. The carboxylated chitosan-bound magnetic nanoparticles can adsorb ionic substances at pH 3-5, but almost no ions are adsorbed at pH 2. This condition may be utilized for the desorption of ions. The adsorption equilibrium of Cu(II) ions is reached within 1 min. Such a fast adsorption rate may be attributed to the absence of internal diffusion resistance.

In addition, the test results for the adsorption of other ions $Ag^+$, $Ni^{2+}$, $Zn^{2+}$, $Cd^{2+}$, $Fe^{3+}$, and $Gd^{3+}$ on the carboxylated chitosan-bound magnetic nanoparticles are shown in Table 1.

TABLE 1

| Metal cations | Initial pH | Recovery (%) |
|---|---|---|
| $Ag^+$ | 5.0 | 96.8 |
| $Ni^{2+}$ | 5.2 | 97.8 |
| $Zn^{2+}$ | 4.3 | 98.7 |
| $Cd^{2+}$ | 6.3 | 99.0 |
| $Fe^{3+}$ | 2.8 | 99.1 |
| $Gd^{3+}$ | 2.0 | >99.5 |

As shown in Table 1, the carboxylated chitosan-bound magnetic nanoparticles of the present invention are suitable for use in adsorbing metal cations.

EXAMPLE 3

The feasibility of carboxylated chitosan-bound magnetic nanoparticles as a magnetic nano-adsorbent for the removal of anionic species from aqueous solutions was demonstrated using acidic dyes such as crocein orange G (AO12) and acid green 25 (AG25) as model compounds. The adsorption experiments were conducted at pH 3-5 under a constant temperature of 25. by mixing a polar solution containing the acidic dyes with the carboxylated chitosan-bound magnetic nanoparticles for adsorbing the acidic dyes. Then, a magnetic field was applied to separate out the carboxylated chitosan-bound magnetic nanoparticles with the acidic dyes adsorbed thereon.

Figure 6:
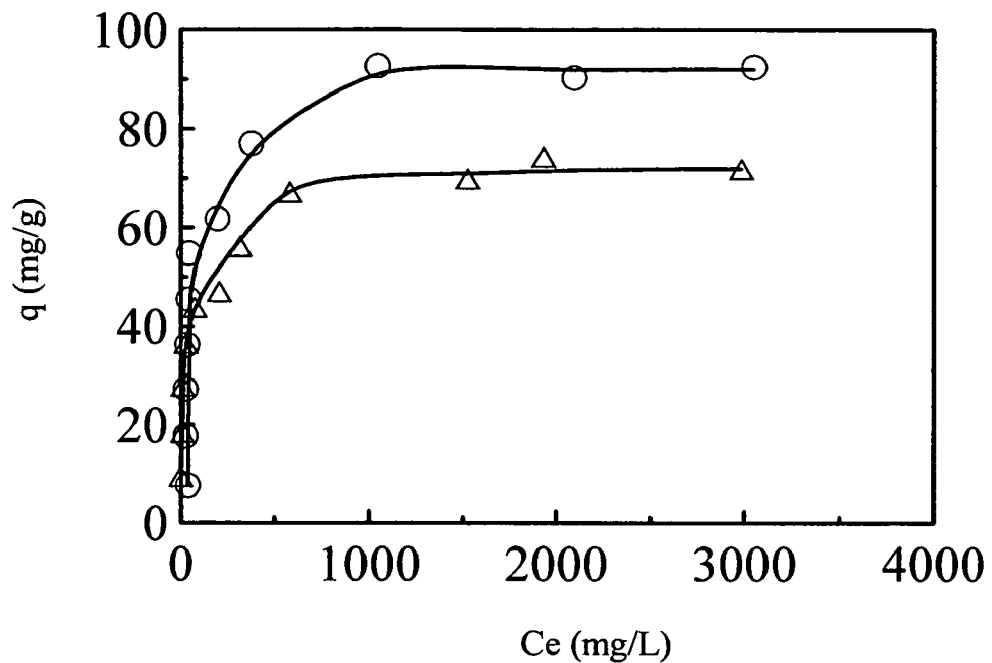
FIG. 6 shows the equilibrium isotherms for the adsorption of acidic dyes on the carboxylated chitosan-bound magnetic nanoparticles.

FIG. 6 shows the equilibrium isotherms for the adsorption of AO12 (as indicated by .) and AG25 (as indicated by .) on the carboxylated chitosan-bound magnetic nanoparticles wherein Ce is the equilibrium concentration in solution (mg/L) and q is the adsorption capacity (mg/g). As shown, the adsorption capacity increases with the initial concentration, the maximum adsorption capacity for AO12 is 1883 mg/g, and the maximum adsorption capacity for AG25 is 1471 mg/g. The carboxylated chitosan-bound magnetic nanoparticles can adsorb anionic species at pH 3-5, but almost no anionic species are adsorbed at pH 6. This condition may be utilized for the desorption of ions.

In addition, the test results for the adsorption of other metal anionic species such as $AuCl_4^-$ and $PdCl_4^{2-}$ on the carboxylated chitosan-bound magnetic nanoparticles are shown in Table 2.

TABLE 2

| Metal anionic species | Initial pH | Recovery (%) |
|---|---|---|
| $AuCl_4$ | 3.1 | 99.4 |
| $PdCl_4^2$ | 2.8 | 99.5 |

EXAMPLE 4

The carboxylated chitosan-bound magnetic nanoparticles act as a carrier for drug molecules or biomolecules.

Figure 7:
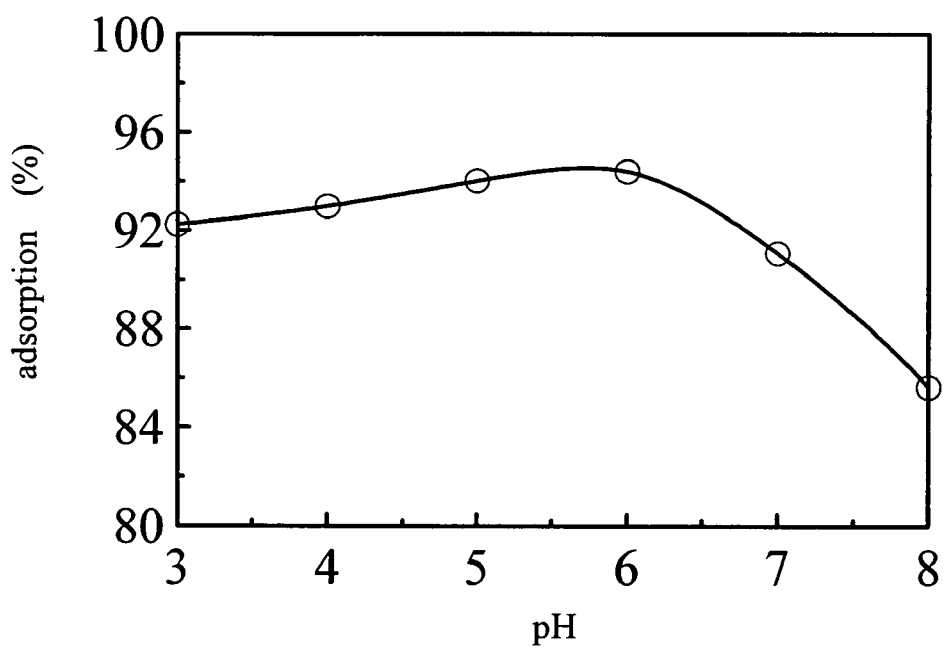
FIG. 7 shows the pH dependence of DOX adsorption on the carboxylated chitosan-bound magnetic nanoparticles.

A polar solution containing the drug molecule such as a solution of anti-cancer drug such as doxorubicin (DOX) was mixed with the carboxylated chitosan-bound magnetic nanoparticles at pH 3-5 under a constant temperature of 25. FIG. 7 shows the pH dependence of DOX adsorption on the carboxylated chitosan-bound magnetic nanoparticles, wherein initial concentration of DOX solution is 100 mg/liter. As shown, DOX and the carboxylated chitosan-bound magnetic nanoparticles form stable conjugate in pH 3-8.

Figure 8:
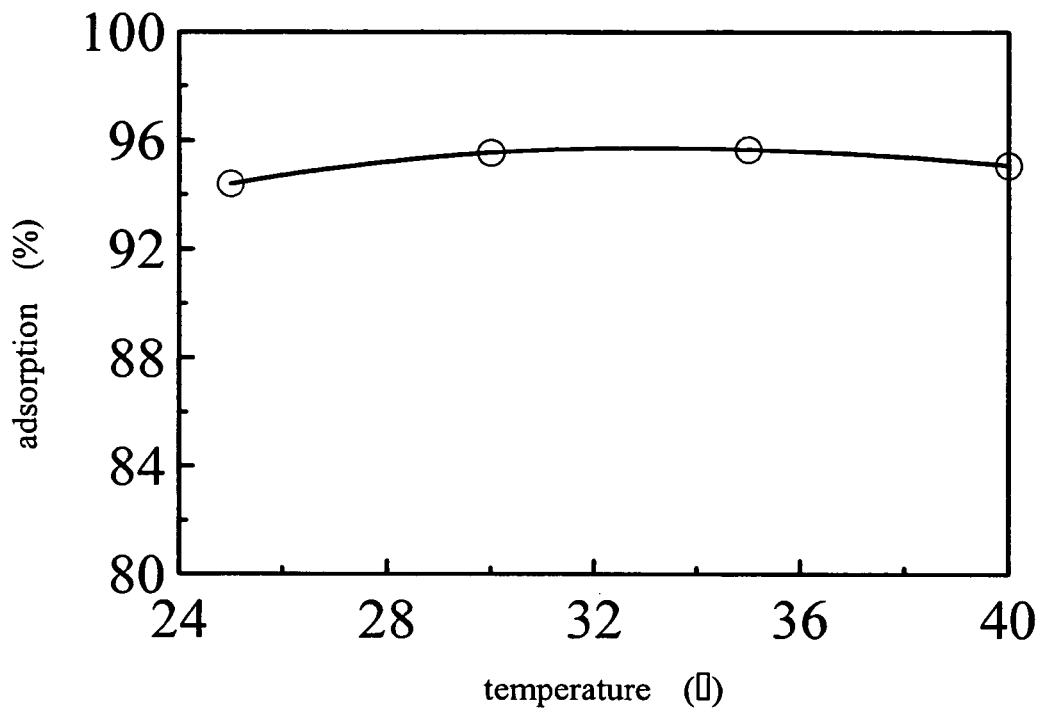
FIG. 8 shows the temperature dependence of DOX adsorption on the carboxylated chitosan-bound magnetic nanoparticles.

FIG. 8 shows the temperature dependence of DOX adsorption on the carboxylated chitosan-bound magnetic nanoparticles, wherein initial concentration of DOX solution is 100 mg/liter. As shown, DOX and the carboxylated chitosan-bound magnetic nanoparticles form stable conjugate in 25.-40.

Figure 9:
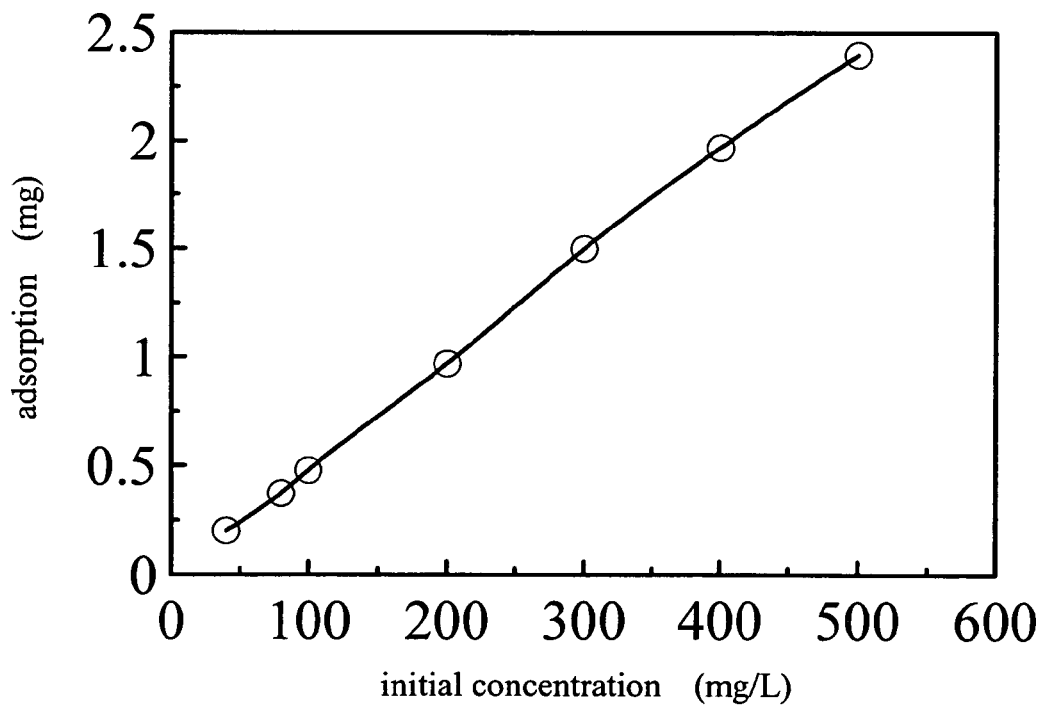
FIG. 9 shows the relationship between the initial DOX concentration and its adsorption amount on the carboxylated chitosan-bound magnetic nanoparticles.

FIG. 9 shows the relationship between the initial DOX concentration and its adsorption amount on the carboxylated chitosan-bound magnetic nanoparticles. As shown, the adsorption amount of DOX increases with the initial DOX concentration, and quite a high adsorption capacity of DOX may be obtained by a high initial DOX concentration.

In addition, the test results for the adsorption of biomolecules such as lipase, bovine serum albumin (BSA), and deoxyribonucleic acid (DNA) on the carboxylated chitosan-bound magnetic nanoparticles are shown in Table 3.

TABLE 3

| Biomolecules | Initial pH | Recovery (%) |
|---|---|---|
| Lipase | 3.0 | 98.8 |
| BSA | 3.0 | 75.5 |
| DNA | 5.0 | 19.8 |

As shown in Table 3, the carboxylated chitosan-bound magnetic nanoparticles form stable conjugate with lipase and BSA. The adsorption result for DNA is not as expected but still acceptable. As is apparent from the results mentioned above, the carboxylated chitosan-bound magnetic nanoparticles of the present invention are suitable for as a biomedical magnetic carrier. In application, a magnetic field may be applied to direct the polysaccharide-bound magnetic nanoparticles with the drug molecules and/or biomolecules adsorbed thereon to a predetermined position in vitro or in vivo.

To sum up, the polysaccharide-bound magnetic nanoparticles of the present invention are highly stable and well dispersed, and possess the advantages of high adsorption capacity, fast adsorption rate, and easy magnetically manipulation. Therefore, they can be used to adsorb many ionic substances such as metal cations, anionic species (such as metal anionic species or acidic dyes), drug molecules or biomolecules, and further act as an adsorbent for wastewater treatment or biochemical separation, a carrier for drugs or gene site-directed delivery, and a magnetic resonance imaging (MRI) contrast agent.

As is apparent from the examples mentioned above, the present invention is characterized in that a carboxylated polysaccharide with various functions such as chelating and ion exchange is covalently bound on the surface of magnetic nanoparticles. The polysaccharide-bound magnetic nanoparticles are highly stable, well dispersed, and have chelating or ion exchange functions. Therefore, they can be used to adsorb many ionic substances such as metal cations, anionic species, drug molecules and biomolecules, and further act as an adsorbent for wastewater treatment or biochemical separation, a carrier for drugs or gene site-directed delivery, and a magnetic resonance imaging (MRI) contrast agent.

As is understood by a person skilled in the art, the foregoing preferred embodiments of the present invention are illustrated of the present invention rather than limiting of the present invention. It is intended to cover various modifications and similar arrangements included within the spirit and scope of the appended claims, the scope of which should be accorded the broadest interpretation so as to encompass all such modifications and similar structure.

What is claimed is:

1. Polysaccharide-bound magnetic nanoparticles, each comprising:
   a magnetic nanoparticle; and
   carboxylated chitosan or derivatives thereof, encapsulating the magnetic nanoparticle.

2. The polysaccharide-bound magnetic nanoparticles according to claim 1, wherein the chitosan, or derivatives thereof, is covalently bound to the surface of the magnetic nanoparticle via a carboxyl group.

3. The polysaccharide-bound magnetic nanoparticles according to claim 1, wherein the polysaccharide-bound magnetic nanoparticles show good monodispersity.

4. The polysaccharide-bound magnetic nanoparticles according to claim 1, wherein the polysaccharides on most of the polysaccharide-bound magnetic nanoparticles are respectively covalently bound to only one magnetic nanoparticle.

5. A method for producing polysaccharide-bound magnetic nanoparticles, comprising the steps of:

forming a magnetic nanoparticle;

providing chitosan or derivatives thereof;

conducting a carboxylation process on the chitosan or derivatives thereof; and covalently binding a carboxylated chitosan or derivatives thereof to a surface of the magnetic nanoparticle through activation with carbodiimide.

6. The method according to claim 5, wherein the covalently binding step further comprises the step of adding the carboxylated chitosan, the magnetic nanoparticle and the carbodiimide to a buffered solution.

7. The method according to claim 6, wherein the buffered solution has a pH in the range of about 6 to about 7.

8. The method according to claim 6, wherein the magnetic nanoparticle is a $Fe_3O_4$ nanoparticle, and the weight ratio of the carboxylated chitosan to the $Fe_3O_4$ nanoparticle in the buffered solution is at least about 0.05.

9. The method according to claim 5, wherein the resulting polysaccharide-bound magnetic nanoparticles show good monodispersity.

* * * * *